United States Patent [19]

Shimamoto et al.

[11] Patent Number: 6,147,230
[45] Date of Patent: Nov. 14, 2000

[54] AMINO ACID DYSIHERBAINE

[75] Inventors: Keiko Shimamoto, Osaka; Ryuichi Sakai; Hisao Kamiya, both of Iwate; Michio Murata, Tokyo, all of Japan

[73] Assignee: Suntory Limited, Osaka, Japan

[21] Appl. No.: 09/077,371
[22] PCT Filed: Sep. 1, 1997
[86] PCT No.: PCT/JP97/03047
§ 371 Date: May 26, 1998
§ 102(e) Date: May 26, 1998

[30] Foreign Application Priority Data

Sep. 27, 1996 [JP] Japan .................................. 8-255673

[51] Int. Cl.[7] ................................................ C07D 311/00
[52] U.S. Cl. ............................................................ 549/396
[58] Field of Search ............................................. 549/396

[56] References Cited

U.S. PATENT DOCUMENTS 4,959,493  9/1990  Ohfume et al. .......................... 562/506

OTHER PUBLICATIONS

J. Am. Chem. Soc. 1997, 119, 4112–4116, Ryuichi Sakai et al., "Dysiherbaine: A New Neurotoxic Amino Acid from the Micronesian Marine Sponge Dysidea Herbacea"

Primary Examiner—Amelia Owens
Attorney, Agent, or Firm—Pillsbury Madison & Sutro LLP

[57] ABSTRACT

The present invention provides a novel amino acid dysiherbaine which is a non-NMDA type glutamate receptor agonist as well as salts and biological precursors thereof, which are useful as experimental materials for elucidating neuronal death or the functions of signal transduction of the central nervous system associated with glutamate receptors and which provide a possibility for the development of a glutamate receptor blocker.

A novel amino acid dysiherbaine represented by the formula (1):

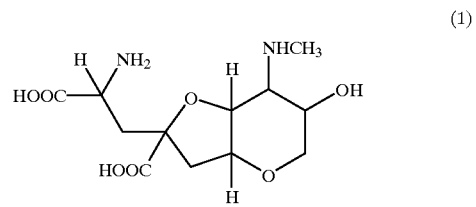

(1)

is obtained by purifying an aqueous extract of a sponge such as *D. herbacea* on the basis of toxicity to mice by liquid chromatography using Sephadex LH20 or the like and HPLC using a C18 column, and optionally converting it into a biological precursor thereof.

3 Claims, No Drawings

AMINO ACID DYSIHERBAINE

FIELD OF THE INVENTION

The present invention relates to a novel glutamate receptor agonist, more specifically a novel amino acid dysiherbaine which is an agonist for non-NMDA type glutamate receptors as well as salts and biological precursors thereof.

PRIOR ART

L-glutamic acid has attracted attention as an excitatory neurotransmitter in central nervous systems of mammals, a neuroexcitotoxin which destroys neurocytes to cause various cerebro-neuropathies, and a substance which has an important role in the formation of memory or learning.

L-glutamate receptors are associated with such a variety of physiological functions and classified into two types, i.e. ionotropic receptors (iGluR) and metabotropic receptors (mGluR). Ionotropic receptors are subclassified based on the recent information on exogenous agonists into the following three subtypes:
(a) NMDA type,
(b) KA type, and
(c) AMPA type
wherein NMDA=N-methyl-D-aspartic acid, KA=kainic acid, AMPA=α-amino-3-hydroxy-5-methyl-4-isoxazolepropionic acid and these abbreviations will be hereinafter sometimes used.

KA type and AMPA type are sometimes collectively called as non-NMDA type.

Among non-NMDA type receptors, KA type receptors are thought to be involved in neuronal death since it has been found that kainic acid itself induces epileptoid lesions and neuronal degeneration in rats. On the other hand, AMPA receptors are considered to be involved in normal rapid transmission in central nervous systems and the activation of AMPA receptors seem to trigger the activation of NMDA type receptors. In recent years, researches on the level of molecular biology have showed that ionotropic L-glutamate receptors types 1–4 (iGluR 1-4) correspond to receptors of AMPA type while types 5-7 (iGluR 5-7) and types KA1, 2 correspond to receptors of KA type.

SUMMARY OF THE INVENTION

As described above, stimulation of glutamate receptors by L-glutamic acid plays an important role in living bodies, including neuronal death and the signal transduction of the central nervous system. Thus, glutamate receptor agonists are experimental materials indispensable for explaining the functions of the nervous system. However, the only known agonists for non-NMDA type (particularly KA type) receptors are kainoids (collective name of the compounds which have a kainic acid skeleton in their molecule) such as naturally occurring domoic acid and acromelic acid. Therefore, there is a demand for development of agonists/antagonists with a new skeleton for use in investigations of the functions of the receptors.

DETAILED DESCRIPTION OF THE INVENTION

Bearing in mind that a number of natural marine products known as poisons can act at micro-doses on systems which are involved in intracellular/intercellular signal transduction, we have made an attempt to isolate a novel compound with a specific physiological activity. As a result, we found that an aqueous extract of a species of Micronesian sponge (*Dysidea herbacea*) induces characteristic conditions such as paroxysmal spasm in mice.

As a result of careful studies to isolate and purify the active substance inducing these conditions on the basis of the above finding, we have succeeded in isolating a novel amino acid represented by the following chemical formula (1):

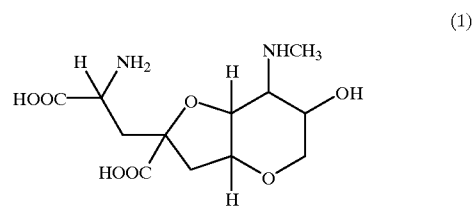

(1)

from an aqueous extract of *D. herbacea* on the basis of toxicity to mice by combining liquid chromatography and high performance liquid chromatography (HPLC). The compound of this structure is an agonist for non-NMDA type glutamate receptors, and named dysiherbaine.

The compound of the chemical formula (1) in the form of a salt or a biological precursor in which one or each of two carboxyl groups forms a lower alkyl ester, for example, will be converted in vivo into dysiherbaine and also shows its biological activity.

Accordingly, the present invention provides a novel amino acid dysiherbaine as well as salts and biological precursors thereof as agonists for non-NMDA type glutamate receptors.

Examples of lower alkyl esters of the compound of the present invention include esters with a straight or branched lower alkyl group containing 1 to 5 carbon atoms, such as methyl ester, ethyl ester, n- and iso-propyl ester, n-, sec- and tert-butyl ester, n-, sec- and tert-pentyl ester, which are obtained by treating dysiherbaine by conventional esterification procedures.

Examples of salts of the compound of the present invention include acid addition salts, alkali metal salts, alkali earth metal salts, etc. which are obtained from dysiherbaine by conventional procedures, and they are preferably physiologically acceptable if used as pharmaceuticals or biochemical reagents or the like. Such acid addition salts include lactate, acetate, succinate, maleate, fumarate, tartrate, citrate, gluconate, ascorbate, benzoate, methanesulfonate, cinnamate, benzenesulfonate, or phosphate, hydrogenphosphate, hydrochloride, hydrobromide, hydroiodide, sulfamate, sulfate and hydrogensulfate, etc. Such alkali metal salts include sodium salt and potassium salt, and alkali earth metal salts include calcium salt.

Compound (1) of the present invention is obtained by purifying an aqueous extract of a sponge containing said compound such as *D. herbacea* on the basis of toxicity to mice by liquid chromatography using Sephadex LH20 or the like and high performance liquid chromatography (HPLC) using a C18 column until a UV absorption monitor at 210 nm shows a single peak.

When intraperitoneally administered to mice, Compound (1) of the present invention induces scratching on the flank at a low dose (20 μg/kg), epileptoid spasm at a moderate dose (1.3 mg/kg) and violent attack leading to death at a higher dose (6.5 mg/kg).

Compound (1) of the present invention inhibits [$^3$H] kainic acid and [$^3$H] AMPA, but not an NMDA antagonist [$^3$H] CGS-19755 (cis-4-phosphonomethyl-2- piperidinecarboxylic acid) binding to synaptic membrane samples prepared from rat brain.

Moreover, Compound (1) induces a stronger inward current than kainic acid in primary cultures of rat cerebral cortex neurocytes. This current induction response is inhibited by a non-NMDA antagonist CNQX (6-cyano-7-nitroquinoxaline-2, 3-dione) but not an NMDA antagonist MK801 ((5R, 10S)-(+) 5-methyl-10,11-dihydro-5H-dibenzo [a, d] cycloheptene-5, 10-imine). This means that Compound (1) is a non-NMDA type glutamate agonist acting on KA and AMPA type glutamate receptors.

Compound (1) of the present invention shows a stronger in vivo activity than a known KA agonist domoic acid, so that it can be used as a useful reagent of non-kainoid non-NMDA type glutamate agonist equally to kainic acid and domoic acid in the field of neuroscience, and promotes investigations of glutamate receptors including preparation of clinical models to provide essential tools to the development of a glutamate blocker.

The following examples further explain the present invention in detail without, however, limiting the same thereto.

EXAMPLES

Example 1

Isolation of Compound (1)

Step 1. Preparation of a crude extract from sponge

Sponges collected at a shoal (at depths of 3–5 m) of Yap, Micronesia in July 1995, D. herbacea (200 g), were homogenized with purified water (20 ml), followed by centrifugation of 10,000 rpm at 4° C., to give an extract. To this extract was added 2-propanol (100 ml) to remove high molecular substances by precipitation and the supernatant from the centrifugation was collected, concentrated under reduced pressure and lyophilized to give a crude extract.

Step 2. Purification of Compound (1)

The obtained crude extract was dissolved in purified water (50 ml) and applied to column chromatography on Sephadex LH20 (Pharmacia, 3.5×100 cm) with purified water as an eluent. Fractions showing toxicity by intraperitoneal administration to mice were collected and applied to reverse phase column chromatography on ODS medium pressure column (Wako Pure Chemicals, WAKO 60) with purified water as an eluent. Active fractions were collected and separated by column chromatography on Sephadex LH20 (Pharmacia, 3.5×100 cm) again. Then, the active fractions were passed at a flow rate of 1 ml/min through HPLC column of RP18 (Bio-Rad, 1×25 cm) with purified water as a developing solvent. Peak fractions eluting at a retention time of about 14.6 minutes were collected while monitoring UV absorption at 210 nm, thus 7 mg of Compound (1) was obtained as a colorless amorphous product. Compound (1) gave a single peak at a retention time of 14.6 minutes during said HPLC and was named dysiherbaine.

Instrumental analyses:

TLC (C-18): Rf=0.7 ($H_2O$), Rf=0.4 (methanol/0.5 M-NaCl=5:1).

$[\alpha]D=-3.5°$ (c 0.4, $H_2O$, 26° C.).

CD ($H_2O$): λext 223 nm, Δε-1.4; λext 203 nm, Δε11.6.

PMR (500 MHz, $D_2O$, δppm): 1.93 (dd, 1H, J=11.5, 15.0 Hz), 2.15 (dd, 1H, J=3.5, 14.0 Hz), 2.58 (dd, 1H, J=0.5, 14.0 Hz), 2.59 (dd, 1H, J=2.5, 15.0 Hz), 2.75 (s, 1H), 3.47 (dd, 1H, J=2.5, 11.5 Hz), 3.54 (dd, 1H, J=1.0, 13.0 Hz), 3.55 (dd, 1H, J=3.5, 3.5 Hz), 3.85 (m, 1H), 3.88 (dd, 1H, J=2.5, 13.0 Hz), 4.15 (brs, 1H), 4.30 (m, 1H).

ESIMS: m/Z 305 ( +H), 327 (M+Na).

HRFABMS: calcd for $C_{12}H_{21}N_2O_7$ 305.1349, found 305.1348.

These data revealed that dysiherbaine is represented by the above chemical formula (1) and an estimated stereoisomeric form of the chemical formula (1a):

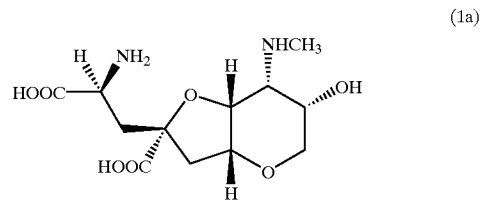

(1a)

Example 2

Synthesis of dysiherbaine dimethyl ester

To a solution of dysiherbaine obtained in Example 1 (2.2 mg) in methanol (0.9 ml) was added an ice-cooled 10% thionyl chloride/methanol solution (100 μl) and the mixture was stirred at room temperature for 24 hours. Methanol was distilled off and the residue was dissolved in water (1 ml), then lyophilized to afford the title compound in a quantitative yield.

Instrumental analyses:

TLC (C-18): Rf=0.7 (methanol/0.5 M-NaCl=5:1).

PMR (500 MHz, $CD_3OD$, δppm): 2.25–2.35 (m, 1H), 2.37 (m, 1H), 2.73 (d, 1H, J=13.5 Hz), 2.82 (m, 1H), 2.87 (s, 1H), 3.62 (d, 1H, J=13 Hz), 3.65 (m, 1H), 3.85–3.88 (m, 6H), 3.89 (brs, 1H), 3.95 (dd, 1H, J=5, 13 Hz), 4.07 (m, 1H), 4.22 (brs, 1H), 4.55 (m, 1H).

Evaluation Example 1

Intraperitoneal administration to mice

Compound (1) was diluted with purified water and intraperitoneally injected into a DDY mouse (male, 15 g). At a low dose (20 μg/kg), the animal was found to repeat scratching on the flank for 10–20 minutes. At a moderate dose (1.3 mg/kg), the animal showed epileptoid spasm and recovered from this condition on the following day. At a higher dose (6.5 mg/kg), however, the animal died in about 40 minutes after violent attack.

Evaluation Example 2

Radiobinding assay in rat brain synaptic membrane samples

Rat brain synaptic membrane samples were prepared according to the described protocols (London, E. D., Coyle, J. T., Mol. Pharmacol. 1979, 15, 492; Murphy, D. E., Snowhill, E. W.; Williams, M., Neurochem. Res. 1987, 12, 775 and Murphy, D. E., Hutchison, A. J., Hurt, S. D., Williams, M., Sills, M. A., Br. J. Pharmacol. 1988, 95, 932). Radioligands and incubation conditions used in the binding assay as well as experimental results are as follows:

KA receptors

[Conditions]: ligand [$^3H$] kainic acid 1 nM; incubation medium 100 mM Tris-acetate buffer (pH 7.1); incubation condition 4° C., 1 hour.

[Results]: Compound (1) concentration-dependently inhibited [$^3H$] kainic acid binding to KA receptors. $IC_{50}$ values of Compound (1), glutamic acid and kainic acid are shown below.

| | |
|---|---|
| Compound (1) | 59 ± 7.8 nM |
| Glutamic acid | 110 ± 18 nM |
| Kainic acid | 4.3 ± 0.5 nM |

AMPA receptors

[Conditions]: ligand [$^3$H] AMPA 5 nM; incubation medium 100 mM KSCN/50 mM Tris-acetate buffer (pH 7.4); incubation condition 4° C., 1 hour.

[Results]: Compound (1) also concentration-dependently inhibited [$^3$H] AMPA binding to AMPA receptors. IC$_{50}$ values of Compound (1), glutamic acid and AMPA are shown below.

| | |
|---|---|
| Compound (1) | 224 ± 22 nM |
| Glutamic acid | 124 ± 41 nM |
| AMPA | 5.6 ± 1.1 nM |

NMDA receptors

[Conditions]: ligand [$^3$H] CGS-19755 10 nM; incubation medium 50 mM Tris-acetate buffer (pH 8.0); incubation condition 4° C., 1 hour.

[Results]: Compound (1) did not inhibit [$^3$H] CGS-19755 binding to NMDA receptors under these conditions.

Evaluation Example 3

Electrophysiological evaluation in primary cultures of rat cerebral cortex neurocytes Glutamate receptors expressed in primary cultures of rat cerebral cortex neurocytes grown for 10–21 days were observed for their receptor response to agonists by an electrophysiological method (patch clamp whole cell method) (Murase, K., Randic, M., Shirasaki, T., Nakagawa, T., Akaike, N., Brain Res. 1990, 525, 84). Compound (1) concentration-dependently induced a strong inward current.

EC$_{50}$ values of Compound (1), kainic acid and AMPA are shown below.

Compound (1) EC$_{50}$=4 μM
 Max response=1.40 nA
AMPA EC$_{50}$=4 μM
 Max response=1.26 nA
Kainic acid EC$_{50}$=40 μM
 Max response=1.31 nA The current induced by Compound (1) was significantly inhibited by CNQX but not by MK801.

These evaluation examples revealed that Compound (1) is a non-NMDA type glutamate receptor agonist.

According to the present invention, a novel amino acid dysiherbaine which is a non-NMDA type glutamate receptor agonist is provided as well as lower alkyl esters and salts thereof. This compound is useful for investigations of glutamate receptors including preparation of clinical models to provide an essential tool for to the development of a glutamate receptor blocker.

The compound of the present invention also promotes investigations of non-NMDA type glutamate receptor agonists to provide a possibility to the development a glutamate receptor blocker which is potentially useful for the therapy of neuropathies such as epilepsy, Huntington's disease and Parkinson's disease or neurodegenerations.

What is claimed is:

1. A novel amino acid dysiherbaine represented by the chemical formula (1):

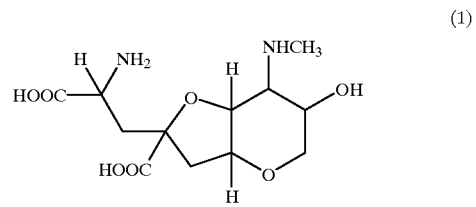

(1)

as well as salts and biological precursors thereof.

2. The compound of claim 1 represented by the chemical formula (1a):

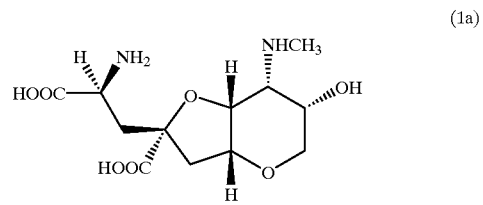

(1a)

as well as salts and biological precursors thereof.

3. An agonist for non-NMDA type glutamate receptors comprising the compound of claim 1 or 2 as an active ingredient.

* * * * *